US006468471B1

(12) United States Patent
Loda et al.

(10) Patent No.: US 6,468,471 B1
(45) Date of Patent: Oct. 22, 2002

(54) SYSTEM FOR, AND METHOD OF, IRRADIATING OPPOSITE SIDES OF ARTICLES WITH OPTIMAL AMOUNTS OF CUMULATIVE IRRADIATION

(76) Inventors: Gary K. Loda, 6921 Johnston Rd., Pleasanton, CA (US) 94566; Richard C. Miller, 4623 Grehadier Pl., Castro Valley, CA (US) 94546

( * ) Notice: Subject to any disclaimer, the term of this patent is extended or adjusted under 35 U.S.C. 154(b) by 0 days.

(21) Appl. No.: 09/710,730

(22) Filed: Nov. 10, 2000

(51) Int. Cl.[7] ............................................... A61L 2/00
(52) U.S. Cl. ............................. 422/22; 422/22; 422/26; 422/28; 422/29; 422/307; 250/453.11; 250/454.11; 250/455.11; 250/492.3
(58) Field of Search .............................. 422/22, 26, 27, 422/28, 307; 250/492.3, 453.11, 454.11, 455.11

(56) References Cited

U.S. PATENT DOCUMENTS 4,788,432 A * 11/1988 Patel ........................ 250/472.1
5,396,074 A * 3/1995 Peck et al. .............. 250/453.11

* cited by examiner

*Primary Examiner*—Robert J. Warden, Sr.
*Assistant Examiner*—Imad Soubra

(57) ABSTRACT

Opposite sides of an article are irradiated to sterilize the article. The cumulative irradiation should be above a first value, and below a second value greater than the first value, at all of the positions in the article to provide the article with desired radiation benefits. Any amount of cumulative radiation between the first and second values is considered as optimal values. For a first range of article thicknesses, the cumulative radiation in the article is at the optimal values. For article thicknesses in a second range greater than in the first range, the cumulative radiation at positions in the article is greater than the optimal values. For article thicknesses in a third range greater than the second range, the cumulative radiation at the different positions in the article is at the optimal values. For the thicknesses in the second range, a member disposed in the radiation path weakens the radiation passing to the article, thereby reducing the cumulative radiation to an optimal value. For each thickness in the second range, a different amount of cumulative radiation above the optimal value may occur when the member is not disposed in the radiation path. The member may accordingly be provided with different thicknesses, dependent upon the amount of the cumulative radiation in the article for the different positions in the second thickness range, to reduce the cumulative radiation in the article to an optimal value. A system may automatically position the member properly for article thicknesses in the second range.

33 Claims, 10 Drawing Sheets

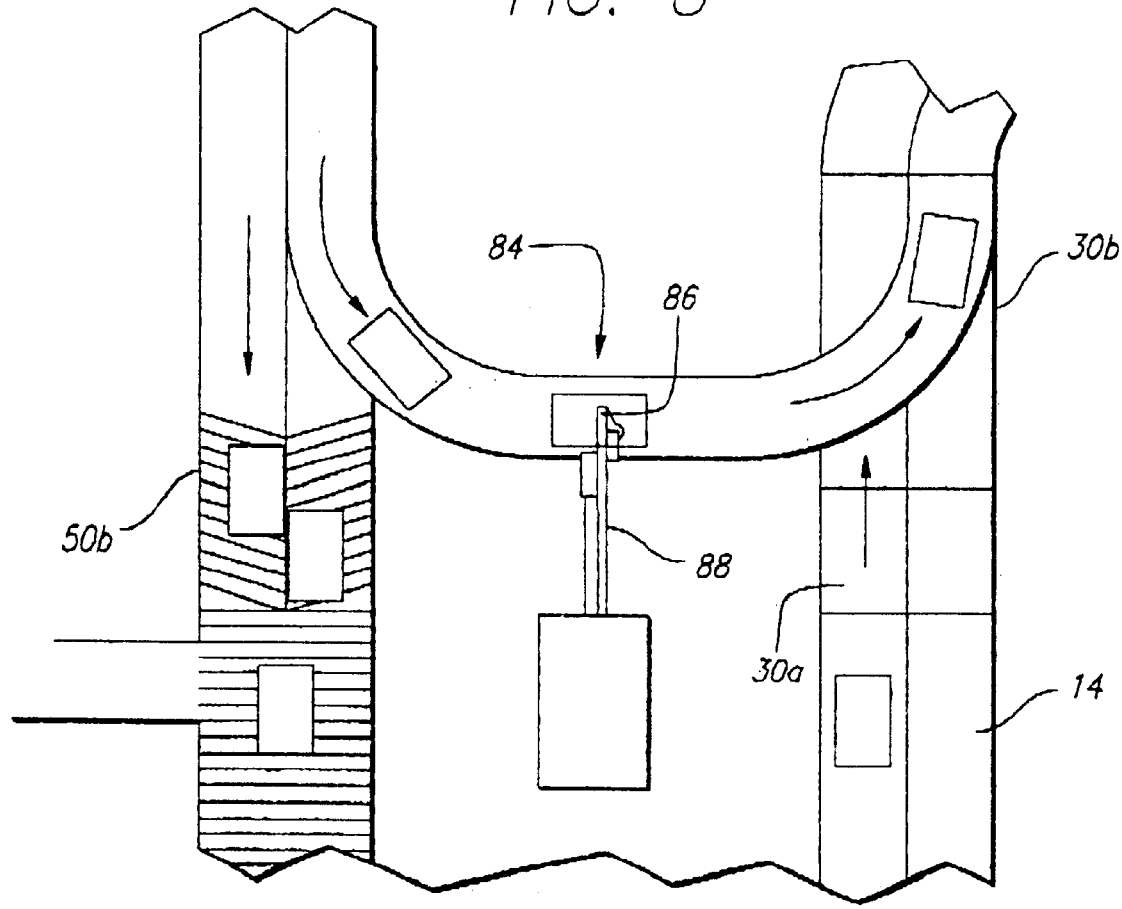

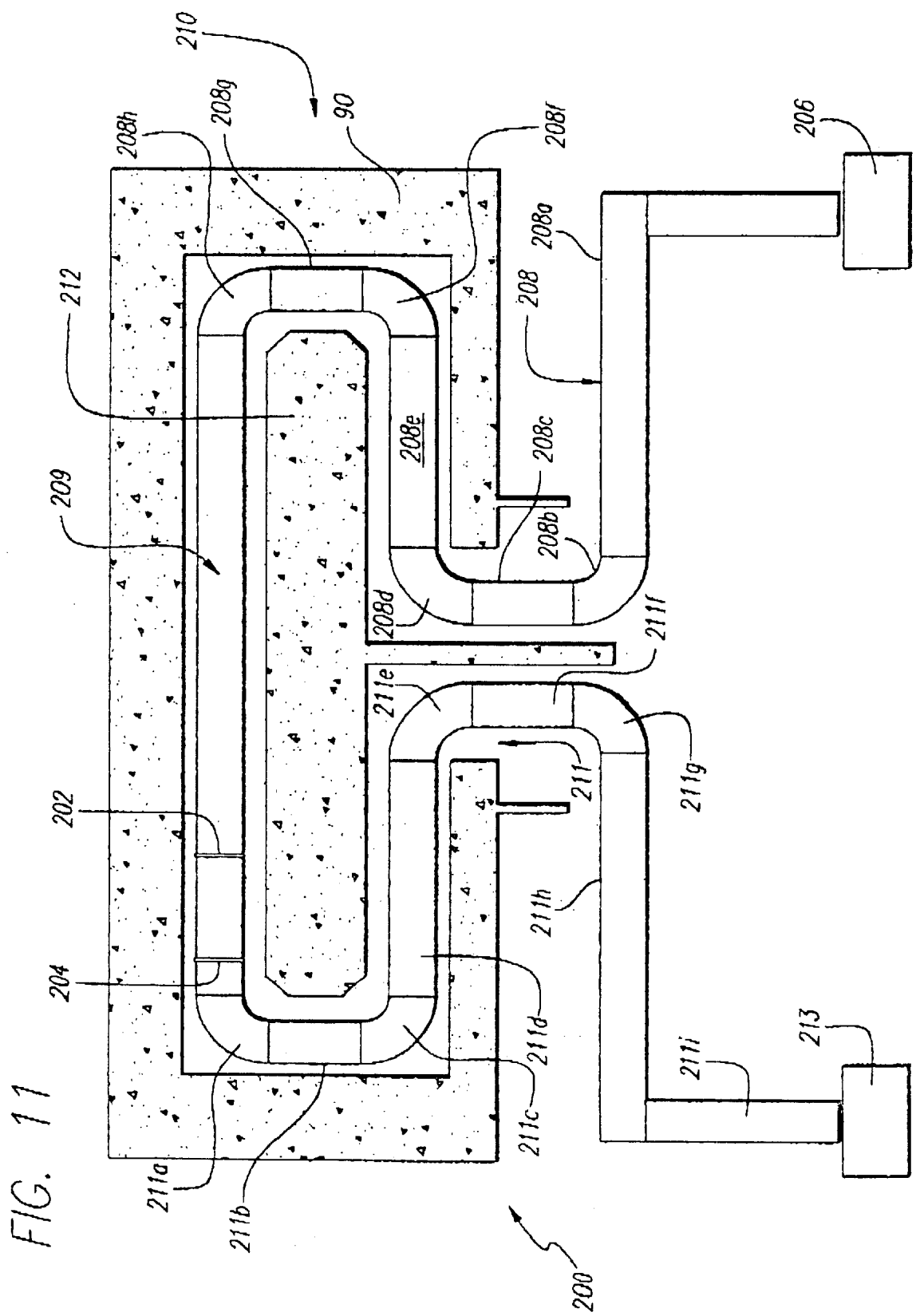

SYSTEM FOR, AND METHOD OF, IRRADIATING OPPOSITE SIDES OF ARTICLES WITH OPTIMAL AMOUNTS OF CUMULATIVE IRRADIATION

This invention relates to systems for, and methods of, irradiating articles, and particularly food articles, to sterilize the articles. The invention particularly relates to systems for, and methods of, irradiating opposite sides of the articles with cumulative irradiation between first and second intensities at all positions in the articles to sterilize the articles.

BACKGROUND OF THE PREFERRED EMBODIMENTS

It has been known for some time that drugs and medical instruments and implements have to be sterilized so that they will not cause patients to become ill from harmful bacteria when they are applied to the patients. Systems have accordingly been provided for sterilizing drugs and medical instruments and implements. The drugs and the medical instruments and implements are then stored in sterilized packages until they are ready to be used.

In recent years, it has been discovered that foods can carry harmful bacteria if they are not processed properly or, even if they are processed properly, that the foods can harbor such harmful bacteria if they are not stored properly or retained under proper environmental conditions such as controlled temperatures. Some of these harmful bacteria can even be deadly.

For example, harmful bacteria have been discovered in recent years in hamburgers sold by one of the large national hamburger chains. Such harmful bacteria caused a number of purchasers of hamburgers from stores in the chain to become sick. As a result of this incident and several other similar incidents, it is now recommended that hamburgers should be cooked to a medium state rather than a medium rare or rare state.

Similarly, harmful bacteria have been found to exist in many chickens that are sold to the public. In view of a number of incidents which have occurred, it is now recommended that all chickens be cooked so that no blood is visible in the cooked chickens.

To prevent incidents such as discussed in the previous paragraphs from occurring, various industries have now started to plan on sterilizing foods before the foods are sold to the public. This is true, for example, of hamburgers and chickens. It is also true of fruits, particularly fruits which are imported from foreign countries.

The food articles are generally irradiated from opposite sides of the articles. The cumulative amount of radiation at every position in the food articles should be at least a first magnitude to insure that all of the harmful bacteria in the articles are destroyed. The cumulative amount of radiation at every position in the articles should be less than a second magnitude to insure that beneficial bacteria in the articles have not been destroyed. The second magnitude is greater than the first magnitude. The range of the cumulative radiation in the articles between the first and second magnitudes may be considered as optimal values of radiation.

The food articles may be provided with different thicknesses. It has been found that the cumulative amount of the radiation is different for different thicknesses of the food articles. For example, flat hamburger patties weighing one-half of a pound (½ lb.) have a different width or thickness in the flat plane than hamburger patties weighing a quarter of a pound (¼ lb.). Because of this, the cumulative amount of the radiation at various positions in the one-half pound hamburgers may be different from the cumulative amount of radiation at different positions in the one quarter pound (¼ lb.) hamburgers.

For a first range of article thicknesses, the amount of the cumulative irradiation in the articles has been at the optimal values. For a second range of article thicknesses greater than the thicknesses in the first range, the cumulative amount of the radiation in the articles has been found to be greater than the optimal value. For a third range of article thicknesses greater than the thicknesses in the second range, the cumulative amount of the irradiation at the different positions in the article has been found to again be at the optimal values.

As will be seen from the discussion in the previous paragraph, a problem exists when the width or thickness of the food articles is in the second range since the cumulative amount of the irradiation at the different positions in the article is greater than the optimal values. The problem is compounded because the thicknesses in the second range are between the thicknesses in the first and third ranges where the cumulative amount of irradiation at the different positions in the articles is at the optimal values.

BRIEF DESCRIPTION OF THE PREFERRED EMBODIMENT

In a preferred embodiment of the invention, opposite sides of an article are irradiated to sterilize the article. The cumulative irradiation should be above a first value, and below a second value greater than the first value, at all of the positions in the article to provide the article with desired radiation benefits. Any amount of cumulative radiation between the first and second values is considered as optimal values.

For a first range of article thicknesses, the cumulative radiation in the article is at the optimal values. For article thicknesses in a second range greater than the first range, the cumulative radiation at positions in the article is greater than the optimal values. For article thicknesses in a third range greater than the second range, the cumulative radiation at the different positions in the article is at the optimal values.

For the thicknesses in the second range, a member disposed in the radiation path weakens the radiation passing to the article, thereby reducing the cumulative radiation to an optimal value. For each thickness in the second range, a different amount of cumulative radiation above the optimal value may occur when the member is not disposed in the radiation path. The member may accordingly be provided with different thicknesses, dependent upon the amount of the cumulative radiation in the article for the different positions in the second thickness range, to reduce the cumulative radiation in the article to an optimal value. A system operative automatically positions the members properly for article thicknesses in the second range.

BRIEF DESCRIPTION OF THE PREFERRED DRAWINGS

In the drawings:

FIG. 8 is a fragmentary plan view of apparatus which may be used in conjunction with the system shown in FIGS. 1–4 for irradiating opposite sides of an article with a single radiating source when the other of the two (2) radiation sources shown in FIG. 1 becomes inoperative;

FIG. 11 is a schematic top plan view of another preferred embodiment of the invention disclosed and claimed in co-pending application Ser. No. 09/456,061 for irradiating opposite sides of an article, and particularly food, with electron beams to sterilize the article;

Figure 15:
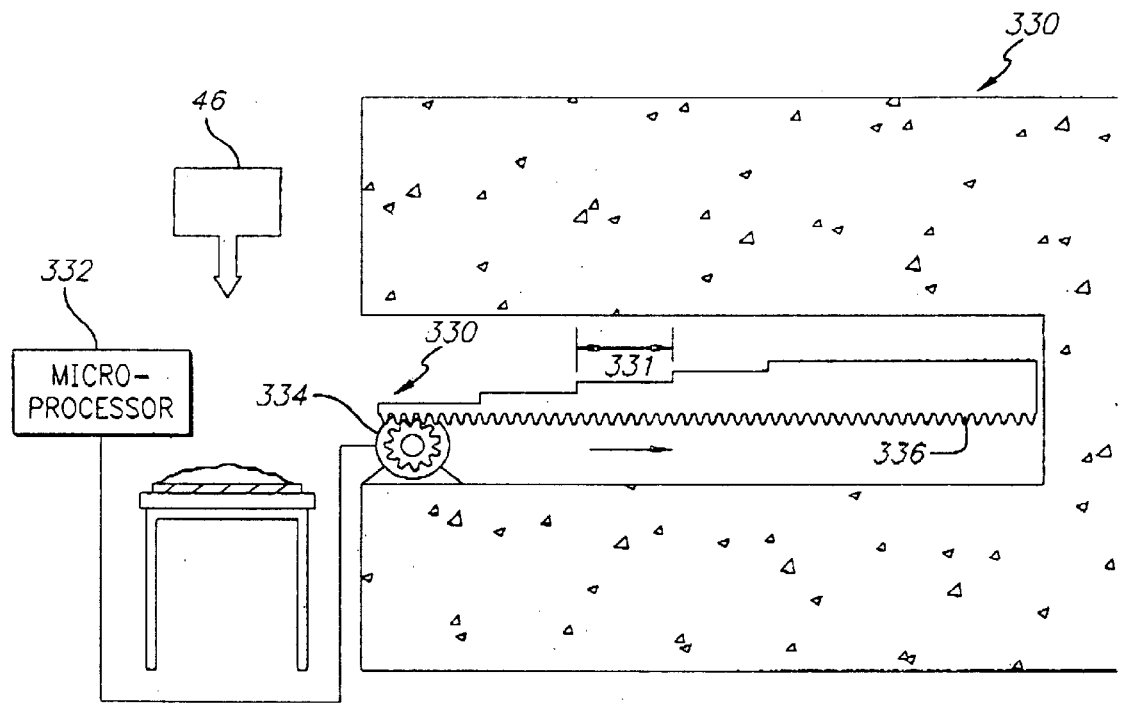
Figure 16:
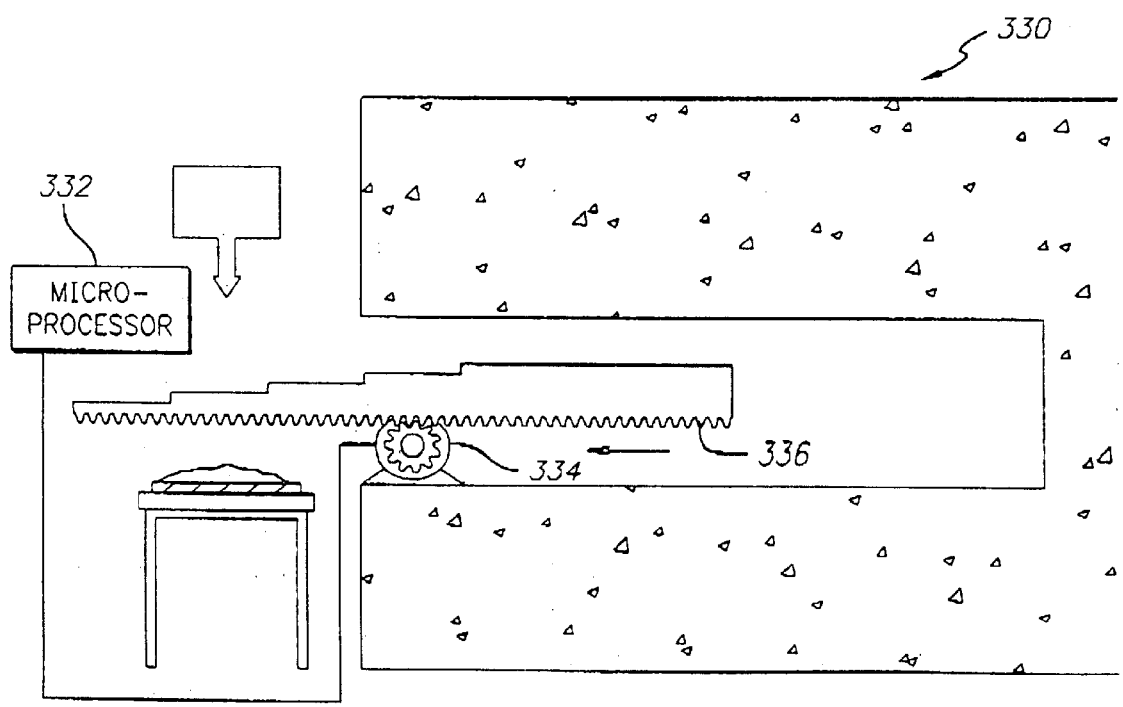

FIG. 15 is a schematic view of a system constituting a preferred embodiment of the invention for automatically positioning the control member between the radiation source and the article to maintain the irradiation in the article within particular limits and shows the member in a non-operative position when the irradiation in the article is within particular limits; and FIG. 16 is another schematic view of the automatic positioning system constituting the preferred embodiment shown in FIG. 15 and shows the disposition of the control member between the radiation source and the article when the irradiation in the article would otherwise be outside of the particular limits.

DETAILED DESCRIPTION OF PREFERRED EMBODIMENTS

The preferred embodiments illustratively incorporate a number of the features disclosed in non-provisional application Ser. No. 09/456,061 filed in the United States Patent and Trademark Office (USPTO) on Dec. 7, 1999, by John Thomas Allen, Gary K. Loda, Russell Parker, George M. Sullivan and Colin Brian Williams for APPARATUS FOR, AND METHOD OF, STERILIZING PRODUCTS, PRIMARILY FOOD PRODUCTS. The preferred embodiments also incorporate a number of the features disclosed and claimed in U.S. Pat. No. 5,396,074 issued to Richard O. Peck, Gary M. Pageau, Colin B. Williams, John T. Allen, Bernard G. Wickersham, Leonard C. Bisgrove and Bruce D. Sellers on Mar. 7, 1995, for an IRRADIATION SYSTEM UTILIZING CONVEYOR-TRANSPORTED CARRIERS and assigned of record to the assignee of record of this application. The preferred embodiments further incorporate features disclosed and claimed in U.S. application Ser. No. 08/854,202 filed on May 9, 1997, in the USPTO in the names of John T. Allen, George M. Sullivan, Michael S. Brazell, Harold B. Knowles, Anthony A. Zante, Richard J. Mendonsa, Richard C. Miller and Kenneth Whitman for ARTICLE IRRADIATION SYSTEM IN WHICH ARTICLE-TRANSPORTING CONVEYOR IS CLOSELY ENCOMPASSED BY SHIELDING MATERIAL and assigned of record to the assignee of record of this application. In addition, the preferred embodiments incorporate features disclosed and claimed in U.S. application Ser. No. 09/102,942 filed in the USPTO on Jun. 23, 1998, for ARTICLE IRRADIATION SYSTEM HAVING INTERMEDIATE WALL OF RADIATION SHIELDING MATERIAL WITHIN LOOP OF CONVEYOR SYSTEM THAT TRANSPORTS THE ARTICLES in the names of John T. Allen, George M. Sullivan and Colin B. Williams as joint inventors and assigned of record to the assignee of record of this application. Reference may be made to U.S. Pat. No. 5,396,074 and/or to any or all of the pending applications specified above to complete the disclosure in this application if the disclosure in this application is found inadequate in any respect.

FIGS. 1–11 in this application respectively correspond to FIGS. 1–11 in co-pending application Ser. No. 09/456,061 specified above. The following description relating to FIGS. 1–11 respectively corresponds to the discussion relating to FIGS. 1–11 in co-pending application Ser. No. 09/456,061. The description referring to FIGS. 1–11 from co-pending application Ser. No. 09/456,061 are intended to provide a background for the preferred embodiments of applicants' invention. It is not intended that the claims in this application should be limited by the specification or drawings in co-pending application Ser. No. 09/456,061.

A preferred embodiment of a system of the invention is generally indicated at 10. The system 10 includes a loading area, generally indicated at 12 (FIG. 1), for receiving articles 14 which are disposed in a stacked relationship in article carriers 16. The articles may illustratively be drugs, drug instruments and/or drug implements. The articles may also illustratively and preferably be meats of various cuts such as hamburgers or may be chickens or fruits or juices or any of a wide variety of other foods. The articles 14 may actually be anything which harbors bacteria that are harmful to humans or animals and that will be destroyed when subjected to irradiation by the system 10. In this way, the system 10 of this invention sterilizes the articles 14 for human or animal use or consumption.

Figure 10:
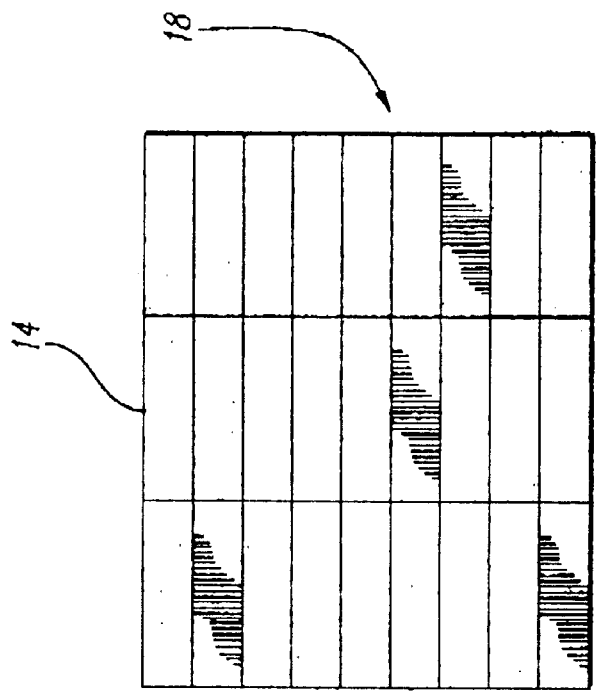
FIG. 10 is an enlarged perspective view of a plurality of articles stacked in a uniform relationship on an article carrier movable on the transport mechanism toward the loading area.
Figure 9:
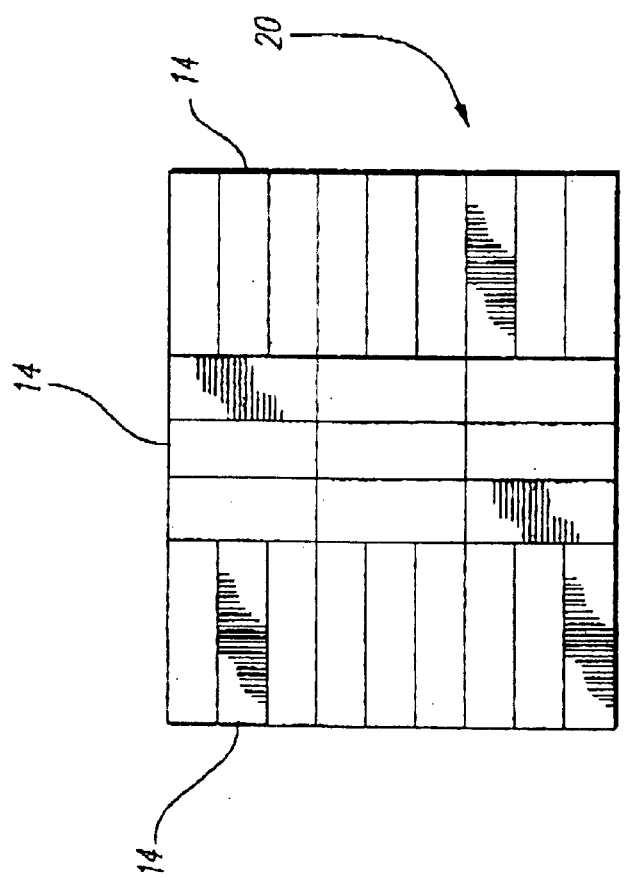
FIG. 9 is an enlarged perspective view of a plurality of articles stacked in a non-uniform relationship on an article carrier movable on a transport mechanism toward the loading area.

The articles may be disposed in the article carriers 16 in a uniformly or non-uniformly stacked relationship. A uniformly stacked relationship of the articles 14 in one of the article carriers 16 is generally illustrated at 18 in FIG. 10. A non-uniformly stacked relationship of the articles 14 in another one of the article carriers 16 is illustrated at 20 in FIG. 10. It will be appreciated that FIGS. 9 and 10 are only illustrative arrangements of the articles 14 in uniformly non-stacked and uniformly stacked relationships.

The article carriers 16 are transported on a transport mechanism generally indicated at 22, past the loading area 12. The direction of movement of the transport mechanism 22 is to the left in FIG. 1 as indicated by an arrow 24. The articles 14 are removed from the article carriers 16 by a robotic assembly 26, generally indicated at 26, which may constitute a Pallet Cell 100/200 apparatus manufactured and sold by FANUC Robotics North America, Inc.

The transfer of the articles 14 from the article carriers 16 by the robotic assembly 26 may be controlled by a controller 28. The controller 28 is programmed to consider the disposition of the individual ones of the articles 14 in the stacked relationship of the articles in the article carriers 16 on the transport mechanism 22 and to operate the robotic assembly 26 in accordance with this stacked relationship whether the stacked relationship be uniform (FIG. 10) or non-uniform (FIG. 9).

When the articles 14 are stacked in a uniform relationship (FIG. 10) in the article carriers 16, the controller 28 causes the robotic assembly 26 to move each of the successive articles 14 in the article carriers 16 in the same path to a load conveyor 30 in the loading area 12 so that each of the articles will have a particular disposition on the loading conveyor. However, when the articles 14 are stacked in the article carriers 16 in a non-uniform relationship (FIG. 9), the controller 28 causes the robotic assembly 26 to move in a path which is adjusted to take account of the non-uniform relationship so that the articles will have the particular disposition on the load conveyor 30.

The load conveyor 30 may transport the articles 14 at a selective speed such as approximately sixty feet per minute (60'/min) to approximately ninety feet per minute (90'/min). The speed of movement of the articles on the load conveyor 30 does not have to be regulated. The load conveyor 30 may be divided into two (2) tracks 30a and 30b of substantially equal widths as by a divider 32. Articles 14 may be simultaneously disposed on each of the tracks 30a and 30b. The articles on each of the tracks 30a and 30b may be the same as, or different from, the articles on the other one of the tracks.

The movement of the articles 14 on the tracks 30a and 30b may be provided by rollers 34 which may be driven by any suitable mechanism known in the art. At the position of transfer of the articles 14 to the load conveyor 30, the rollers 34 may have a herringbone configuration as indicated at 34a. In this configuration, separate rollers 34 may be disposed in each of the tracks 30a and 30b in an angled relationship to the rollers in the other track so that the end of the rollers adjacent the divider 32 is ahead of the end of the rollers distant from the divider in the direction of movement of the articles on the tracks.

In this way, the rollers 34 with the herringbone configuration 34a tend to displace the articles 14 from positions adjacent the divider 32 to positions displaced from the divider. This is desirable to insure that the movement of the articles 14 on the load conveyor 30 will not be impeded by bumping against the divider 32. When the articles have been sufficiently displaced laterally from the divider 32, the rollers are preferably provided with a configuration 36 in which the rollers are substantially perpendicular to the divider 32 and are substantially parallel to one another.

The load conveyor 30 may be formed from a plurality of segments 36a, 36b, 36c, 36d, 36e, 36f and 36g, all of which are preferably disposed in a horizontal plane. The segments 36a, 36b, 36d and 36f may preferably constitute straight segments. The straight segments 36a, 36b and 36f may be disposed in a first direction and the straight segment 36d may be disposed in a second direction substantially perpendicular to the segments 36a, 36b and 36f. The segments 36c, 36e and 36g may constitute curved segments each having a curvature of substantially 90°. The curved segment 36c joins the straight segments 36b and 36d; the curved segment 36e joins the straight segments 36d and 36f; and the curved segment 36g is contiguous to the straight segment 36f.

A process conveyor generally indicated at 38 and having a horizontal disposition in the same plane as the load conveyor 30 is contiguous at one end to the curved segment 36g of the load conveyor 30. The process conveyor 38 is constructed to move the articles 30 at a particular speed such as in the range of approximately thirty feet per minute (30'/min) to approximately sixty feet per minute (60'/min). This speed is preferably regulated by the controller 38 so that it is maintained within particular limits. If the speed should vary from these limits, the radiation applied to the articles 14 on the process conveyor 38 may be interrupted and the operation of the process conveyor may be discontinued.

The process conveyor 38 may be divided into two (2) tracks 38a and 38b, as by a divider 40, in a manner similar to the division of the load conveyor 30 into the two (2) tracks 30a and 30b by the divider 32. The process conveyor may be provided with rollers 42 having a construction similar to the rollers 34 in the load conveyor 30. The rollers 42 at the end of the process conveyor 38 adjacent to the load conveyor segment 36g has a herringbone configuration 42a. The herringbone configuration 42a of the rollers 42 differs form the herringbone configuration 34a of the rollers 34 in that the ends of the rollers 42 distal from the divider 40 lead the end of the rollers adjacent the divider in the direction of movement of the articles 14 on the rollers. The rollers 42 accordingly operate to move the articles 14 on the tracks 38a and 36b to positions contiguous to the divider 40.

The process conveyor is preferably divided into three (3) segments 39a, 39b and 39c (FIG. 4), in the direction of movement of the articles 14 on the tracks 38a and 38b, to form a gap 44a between the segments 39a and 39b and to form a gap 44b between the segments 39b and 39c. The segments 39a, 39b and 39c may respectively and illustratively have lengths of approximately three feet (3'), ten feet (10') and two feet (2'). The gaps 44a and 44 may illustratively have lengths of approximately one half of one foot (½') in the direction of movement of the articles 14 on the process conveyor 38. It will be appreciated that the articles 14 should preferably have a length greater than the lengths of the gaps 44a and 44b so that the articles will be simultaneously on the segments 39a and 39b as they traverse the gap 44a and the articles will be simultaneously on the segments 39b and 39c as they traverse the gap 44b.

A radiation source 46 (FIG. 1) may be disposed to direct radiation through the gap 44a to the articles 14 on the process conveyor 38. The radiation source 46 may be disposed in a vertical direction above the process conveyor 38 to direct light downwardly on the articles 14 on the process conveyor. Similarly, a radiation source 48 may be disposed below the process conveyor 38 to direct radiation upwardly through the gap 44b to the articles 14 on the process conveyor 38. In this way, the radiation will be directed against the opposite sides of the articles 14 on the process conveyor 38. The intensities of the radiation from the sources 46 and 48 should preferably be substantially equal within particular limits.

The radiation sources 46 and 48 preferably provide an electron beam against the opposite sides of the articles 14 on the process conveyor 38. Each of the radiation source 46 and 48 preferably provides an electron beam with an intensity of approximately ten (10) Mev. However, the beam can be of any intensity to kill harmful bacteria in the articles 14 being irradiated without killing beneficial bacteria in such articles. It will be appreciated that other types of radiation sources than those providing electron beams may be satisfactory, particularly in special situations. For example, gamma rays (as from cobalt or cesium) and X-rays may be satisfactory, particularly in specific instances. However, electron beams are generally preferred since they heat the articles only through a minimal range of temperatures and since the electrons directed toward the beams are only temporary in duration. For example, the temperature increase of beef patties when irradiated with an electron beam may be approximately 2° F. This allows frozen beef patties to remain frozen during and after the irradiation of the beef patties.

Electron beam radiation has a number of advantages, particularly for irradiating food, in addition to those discussed in the previous paragraph. These additional advantages include high dose rate, the ability to turn the radiation sources instantaneously on and off, the ability to regulate the irradiated area as by beam scanning, no source replenishments, the ability to regulate the strength of the radiation and the ability to operate in a dual mode (electron beam and X-ray). Other advantages of electron beam irradiation are relatively short exposure time, high power utilization in the fraction of the emitted energy usefully absorbed in the article being irradiated, simplified conveyor systems for the articles (e.g. the articles 14) because of the irradiation of individual articles rather than pallet-sized or tote-size loads and a minimization in the numbers (only 1 or 2) of passes of the articles 14 through the target region of the radiation source(s).

There are certain definite advantages to converging the articles on the tracks 38a and 38b toward the divider 40 on the process conveyor before the articles 14 reach the radiation sources 46 and 48. By converging the articles 14 toward the divider 40, the widths of the radiation from each of the radiation sources 46 and 48 are minimized. This minimizes the consumption of energy in the radiation sources 46 and 48. Alternatively, it provides for an increase in the energy directed by the radiation sources 46 and 48 against the articles 14 on the process conveyor 38.

As previously indicated, the speed of movement of the articles 14 on the load conveyor 30 is preferably greater than the speed of movement of the articles on the process conveyor 38. If the proper ratio of speeds is selected (depending on the lengths of the articles 14), the spacing between successive articles on the process conveyor is minimized, thereby increasing the efficiency in the operation of the system and decreasing the amount of power not utilized.

Figure 1:
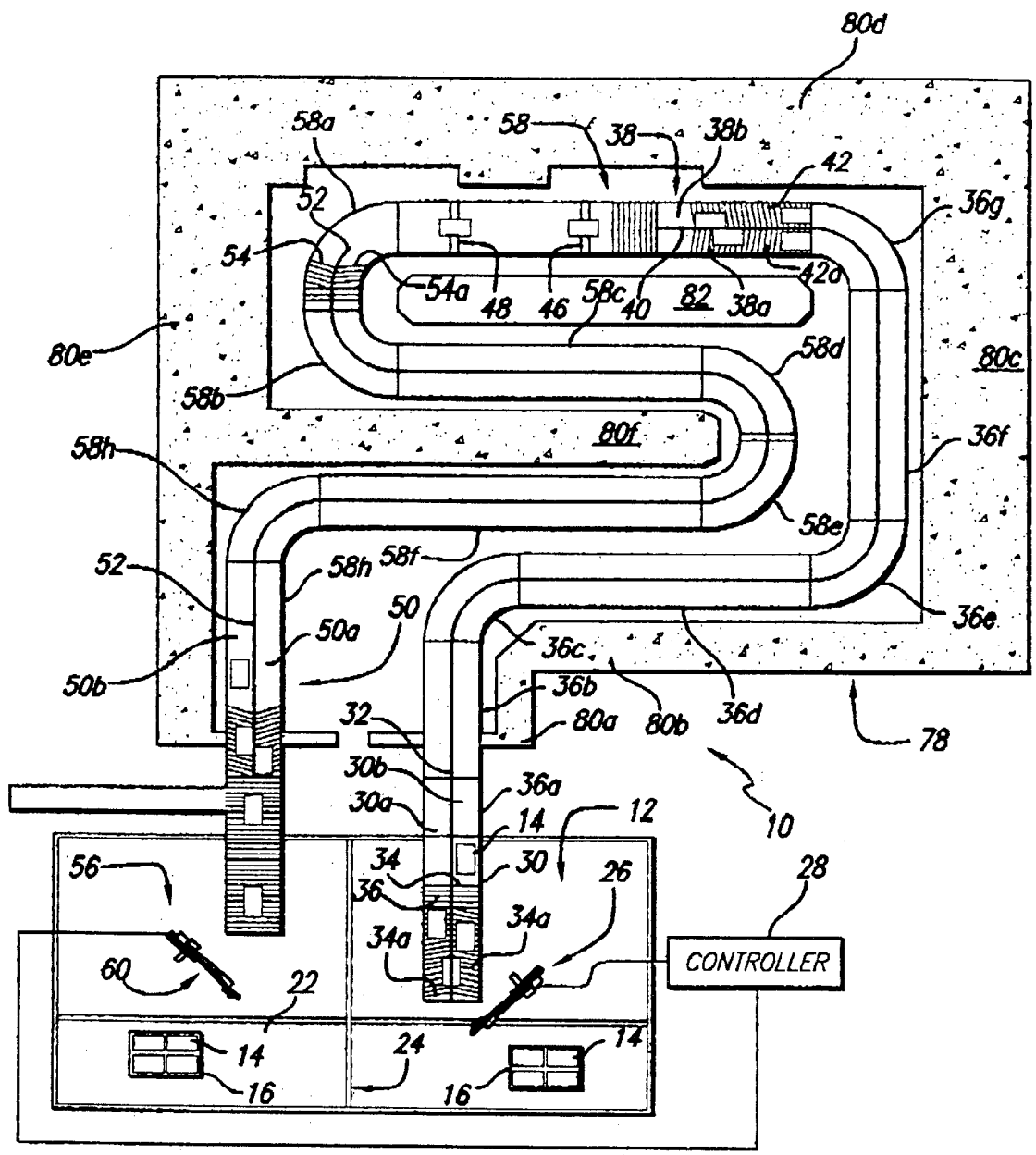
FIG. 1 is a top plan of a system disclosed and claimed in the co-pending application Ser. No. 09/456,061 for irradiating opposite sides of articles, and particularly foods, with electron beams to sterilize the articles.
Figure 2:
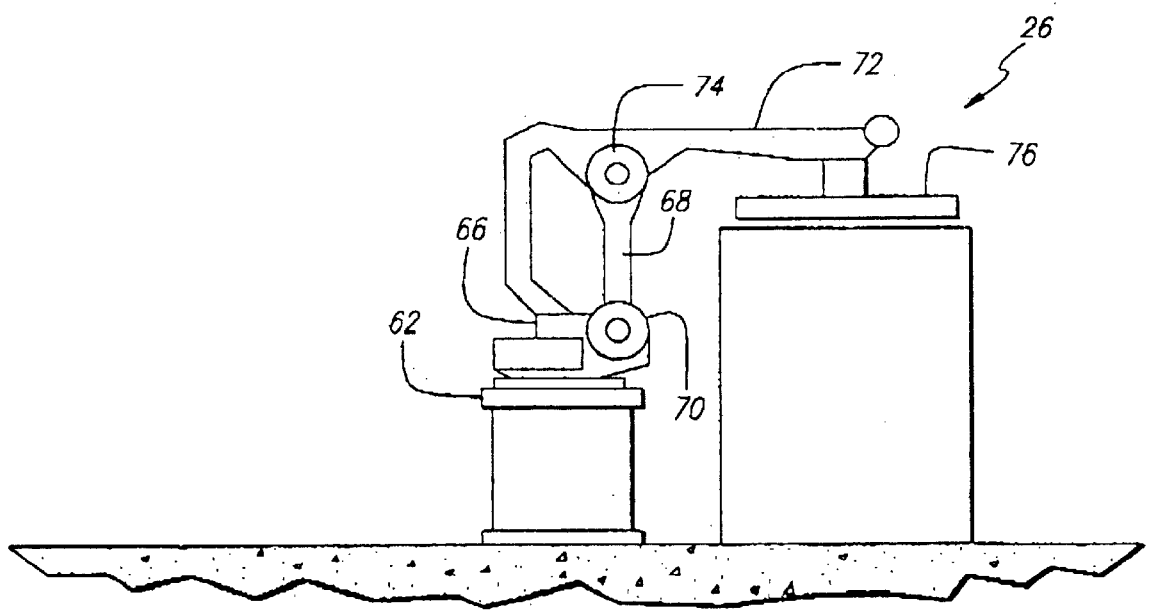
FIG. 2 is an elevational view of one of two (2) robotic assemblies included in the embodiment shown in FIG. 1 and disclosed and claimed in co-pending application Ser. No. 09/456,061, one for transferring the articles from a loading area to a first load conveyor and the other for transferring articles from a second load conveyor to an unloading area.
Figure 3:
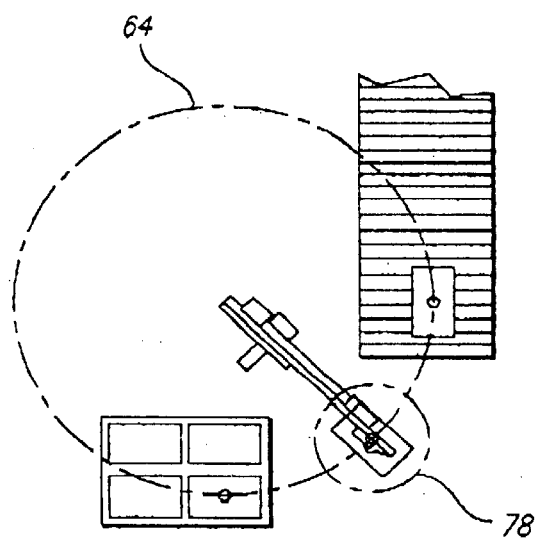
FIG. 3 is a top plan view of the robotic assembly shown in FIG. 2.

The articles 14 on the process conveyor 38 are transferred to a load conveyor generally indicated at 50 (FIG. 1). The load conveyor 50 may have a construction similar to that of the load conveyor 30. For example, a divider 52 may be provided to divide the load conveyor 50 into two (2) tracks 50a and 50b and rollers 54 may be provided on the load conveyor to advance the articles 14 on the load conveyor toward an unloading station generally indicated at 56. The rollers 54 adjacent the process conveyor 38 may be provided with a herringbone configuration 54a similar to the herringbone configuration 34a of the rollers 34. This facilitates the movement of the articles on the load conveyor 50. The resultant separation of the articles 14 on each of the tracks 50a and 50b at the unloading station 56 facilitates the separate and individual handling of the articles at the unloading station.

The load conveyor 50 may be formed from several segments 58a, 58b, 58c, 58d, 58e, 58f, 58g and 58h. The segment 58a is contiguous to the process conveyor 30 and is curved. The segment 58b is contiguous to the segment 58c and is also curved. However, the segments 58a and 58b have opposite curvatures so that the articles 14 passing from the segment 58b travel in an opposite direction through the segment 58c relative to the direction in which the articles pass from the process conveyor 38 to the segment 58a. The segment 58c is a straight segment parallel to the process conveyor 38. The segments 58d and 58e cumulatively provide a curvature of 180° in a manner corresponding to the segments 58a and 58b. The segment 58f is straight and is parallel to the segment 58c but extends in a direction opposite to the direction of the segment 58c. The segment 58g provides a curvature of 90° between the segments 58f and 58h. The segment 58h extends in a direction parallel, but opposite, to the segment 36a in the load conveyor 30. The segment 58h extends to the unloading area 56.

A robotic assembly generally indicated at 60 may be disposed in the unloading area 56 to receive the articles 14 from the load conveyor 50 and to transfer the articles to the article carriers 16 on the transport mechanism 22. The article carriers 16 may constitute those from which the articles 14 have been previously transferred to the load conveyor 30 in the loading area 12. Because of this, the article carriers 16 adjacent to the unloading area 56 are empty. The articles 14 may be transferred to the load conveyor 50 in the unloading area 56 in a uniform relationship such as indicated at 18 in FIG. 10 or in any other uniform relationship or in a non-uniform relationship such as indicated at 20 in FIG. 9 or in any other non-uniform relationship. The transfer of the articles 14 from the load conveyor 50 to the article carriers 16 on the transport mechanism 22 in the uniform or non-uniform relationship may be under the control of the controller 28. The robotic assembly 60 in the unloading area 56 may correspond in construction to the robotic assembly 26 in the loading area 12.

Figure 4:
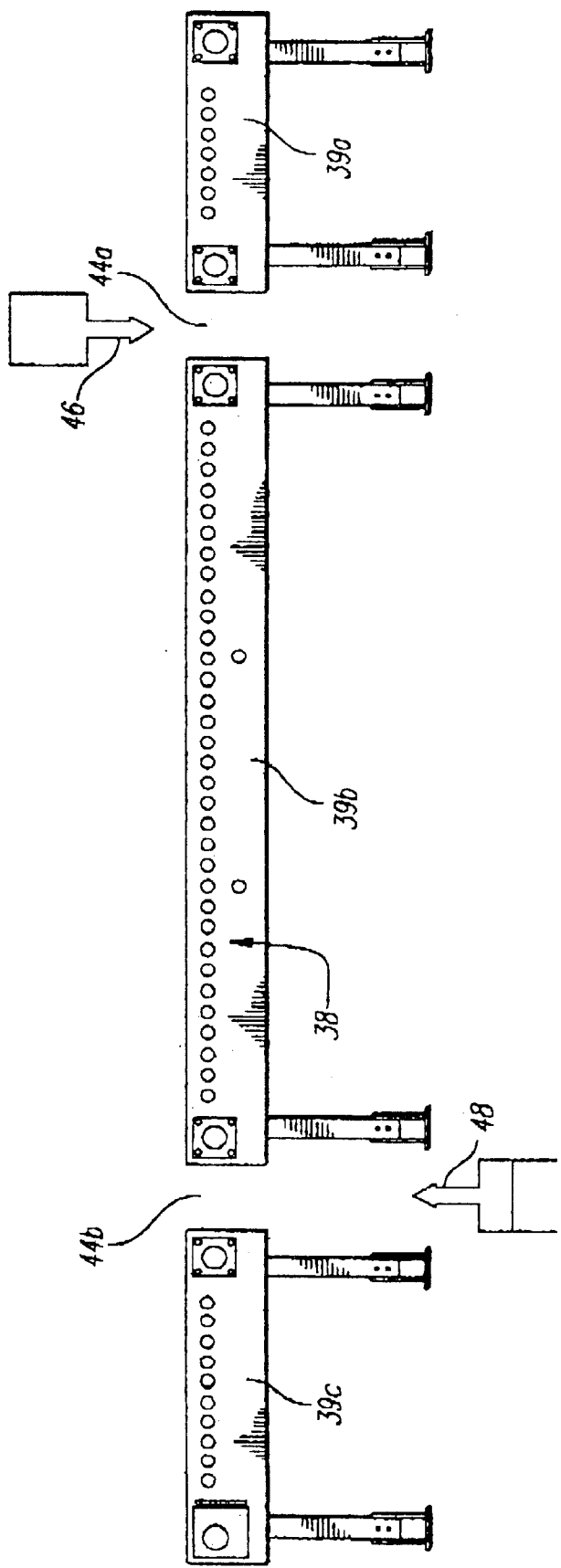
FIG. 4 is a top plan view of a process conveyor included in the system shown in FIGS. 1–3 and disclosed and claimed in co-pending application Ser. No. 09/456,061.

The robotic assembly 26 includes a platform 62 (FIGS. 3 and 4) which is rotatable in a horizontal plane through an annulus indicated at 64 in FIG. 4. A support member 66 extends upwardly from the platform 64. An arm 68 is pivotable in a vertical plane on a pin 70 as a fulcrum, the pin being disposed on the support member 66. A strut 72 supported on the arm 68 is pivotable in a vertical plane on a pin 74. A plate 76 is supported by the strut 70 for a rotary movement in a horizontal plane through an annulus indicated at 78 in FIG. 4.

The platform 62 rotates in the horizontal plane to a position for disposition of the arm 68 in contiguous relationship to one of the articles 14 in one of the article carriers 16 on the transport mechanism 22. The arm 68 is then pivoted on the pin 70 as a fulcrum to provide for the plate 74 to lift the article 14 from the article carrier 16. The platform 62 is then rotated through a horizontal plane to the position of the load conveyor 30. The plate 76 is thereafter rotated to the position for depositing the article 14 in a properly aligned relationship on the load conveyor 30. The strut 72 is then pivoted downwardly on the pivot pin 74 as a fulcrum to deposit the article in the properly aligned relationship on the load conveyor 30.

The inclusion of the two (2) tracks in each of the load conveyor 30, the process conveyor 38 and the load conveyor 50 provides certain important advantages. It allows the articles 14 to be moved past the radiation sources 46 and 48 at one half (½) of the speed at which the articles 14 would move if only one (1) track were provided. A reduced speed is desirable because it simplifies the operation of the irradiating system 10. Another advantage of providing the two (2) tracks in each of the load conveyor 30, the process conveyor 38 and the load conveyor 50 is that one type of article 14 can be processed on one of the tracks at the same time that another type of article can be processed on the other track.

The inclusion of the radiation sources 46 and 48 to apply radiation respectively from positions above and below the articles 14 also provides certain important advantages. One advantage is that the use of the radiation sources 46 and 48 minimizes the time for processing the articles 14. Another advantage is that the thickness of the article 14 being sterilized in each pass can be increased without increasing the intensity of the radiation from the sources 46 and 48.

A further advantage is that the article 14 does not have to be inverted in order to apply radiation to the second opposite side of the article 14. Inverting the article 14 is undesirable when products such as fresh meat patties are being pasteurized. This results from the fact that blood from what was originally the bottom side of the article 14 flows to what was originally the top side of the article when the article is inverted. This blood discolors the visual appearance of the article 14 when the article is again inverted so that what was originally the top side of the article again becomes the top side of the article.

Radiation shielding generally indicated at 78 in FIG. 1 may be applied to the system 10 (a) to limit the existence of radiation from the radiation sources 46 and 48 in areas other than the target region where the articles 14 are to be irradiated and (b) to prevent radiation from the sources from reaching the loading area 12 and the unloading area 56. The radiation shielding 78 may be formed from a suitable material such as concrete. The radiation shielding 78 may encompass the system 10 and may include (a) a portion 80a adjacent the load conveyor segment 36b, (b) a portion 80b adjacent the load conveyor segments 36c, 36d and 36e, (c) a portion 80c adjacent the load conveyor segments 36e, 36f and 36g, (d) a portion 80d adjacent the load conveyor segment 36g, the process conveyor 38 and the load conveyor segment 58a, and (e) a portion 80e adjacent the load conveyor segments 58a, 58b, 58g and 58h. The radiation shielding segments 80a–80e are integral or continuous with one another. A radiation shielding portion 80f integral with the radiation shielding portions 80a–80e extends into the space between the load conveyor segments 58c and 58f.

A radiation shielding member 82 made from a suitable material such as concrete and separated from the radiation shielding portions 80a–80f is disposed in the region between the process conveyor 38 and the load conveyor segment 58c. The radiation shielding member 82 limits the amount of radiation passing to the radiation shielding portions 80a–80c and 88e and accordingly provides for a decrease in the thickness of these radiation shielding portions. The radiation shielding portions 80a–80f and the radiation shielding member 82 are preferably integral with a floor (not shown) made from a suitable material such as concrete and a roof (not shown) made from a suitable radiation shielding material such as concrete. In this way, the system 10 is disposed within an enclosure made from a radiation shielding material such as concrete.

As previously described, the articles 14 may travel on the two tracks 30a and 30b of the load conveyor 30 from the loading area 12, then on the two (2) tracks 38 and 38b of the process conveyor 38 and then on the two (2) tracks 50a and 50b of the load conveyor 50 to the unloading area 56. During the movement of the articles 14 on the process conveyor 38, each of the radiation sources 46 and 48 irradiates the articles 14 on the two tracks 38 and 38b. However, it may sometimes happen that one of the radiation sources 46 and 48 may be inoperative to irradiate the articles 14 on the tracks 38a and 38b of the process conveyor 38. Assume that it is the radiation source 46. Under such circumstances, the other one of the radiation sources 46 and 48 (assume that it is the source 48) performs a double duty and irradiates the two (2) opposite sides of the articles 14 on the tracks 38a and 38b of the process conveyor 38.

To provide for the radiation source 48 to irradiate the two (2) opposite sides of the articles 14, an alternative load conveyor (one track wide), generally indicated at 84 in FIG. 8, is provided between the first track 50a of the load conveyor 50 and the second track 30b of the load conveyor 30. The path of travel of the articles 14 is then the first track 30a of the load conveyor 30, the first track 38a of the process conveyor 38 and the first track 50a of the load conveyor 50. During this path of travel, the first side of the articles 14 is irradiated by the radiation source 48.

The articles 14 then travel from the first track 50a of the load conveyor 50 through the alternate load conveyor 84 (one track wide) to the second track 30b of the load conveyor 30. During this travel, the articles 14 reach a barrier 86. To surmount this barrier, a lifting mechanism 88 is provided to lift the articles from the side of the barrier 86 adjacent the load conveyor 50 to the side of the barrier adjacent the load conveyor 30. While the articles 14 are being lifted above the barrier 86, they are inverted. The articles 14 then travel from the second track 30b of the load conveyor 30 to the second track 38b of the process conveyor 38, then to the second track 50h of the load conveyor 50 and then to the unloading area 56. The radiation source 48 irradiates the second opposite side of the articles 14 during this second movement of the articles 14 past the radiation source 48. The same paths as described above in this paragraph and the previous paragraph are provided when the radiation 48 is unable to irradiate the articles 14 and the radiation source 46 irradiates the two (2) opposite sides of the articles.

Figure 5:
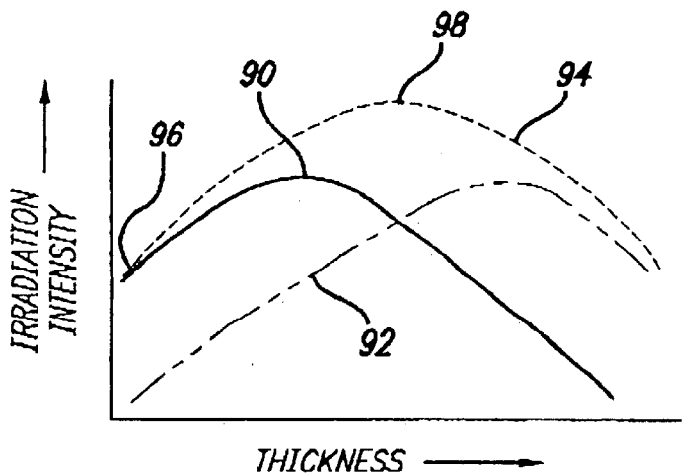
FIG. 5 shows curves illustrating the intensity of the irradiation from opposite sides of an article at progressive distances through the article and illustrating the cumulative intensity of the radiation produced in the article at the progressive distances through the article.

A curve 90 in FIG. 5 shows the irradiation intensity produced in the article 14 at different depths in the article when radiation is provided from the source 46 downwardly on the article. As will be seen, the irradiation intensity increases for some distance downwardly from the top of the article 14 until it reaches a maximum value and then the irradiation dose decreases from that maximum value with further progressive distances downwardly through the article. FIG. 5 also shows an irradiation intensity 92 produced in the article 14 by the source 48. As will be seen, the irradiation intensity from the source 48 increases for a particular distance upwardly through the article 14 from the bottom of the article to a maximum value and then decreases from that maximum value with further progressive distances upwardly through the article. The curve 92 may be considered as an inverse of the curve 90.

A curve 94 in FIG. 9 constitutes a composite of the curves 90 and 92. The composite curve 94 in FIG. 9 has a radiation intensity 96 at the top of the article 14. This corresponds substantially to the radiation intensity at the top of the article 14 for the curve 90. The intensity of the radiation in the composite curve 94 then increases from the dose 96 to a maximum value 98 at a position approximating in the article 14 the position at which the curve 90 has an irradiation intensity corresponding to the irradiation intensity in the curve 92.

Figure 6:
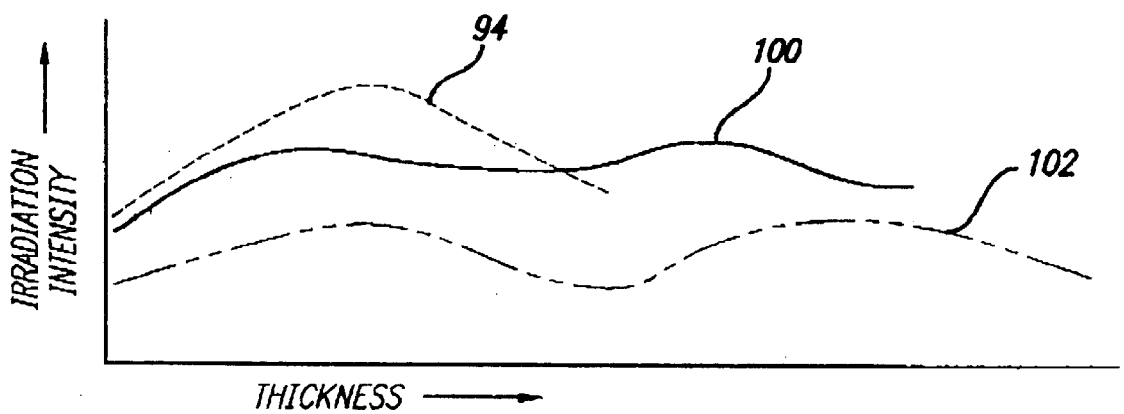
FIG. 6 shows curves illustrating the cumulative intensity of the irradiation at progressive distances through the article when the distance between the opposite sides of the article is varied.

FIG. 6 illustrates composite curves for progressive increases in the thickness of the article 14. The composite curve 94 in FIG. 5 is repeated in FIG. 6. A curve 100 in FIG. 10 constitutes a composite of the radiation intensities produced by the sources 46 and 48 when the thickness of the article 14 is increased by a first amount from the thickness of the article in the composite curve 94. A curve 102 constitutes a composite of the radiation intensities produced by the radiation sources 46 and 48 when the thickness of the article 14 is increased by a second amount greater than the first amount from the thickness of the article 14 for the composite curve 94. As will be seen for each of the composite curves 100 and 102, the difference between the maximum and minimum radiation intensities changes as the thickness of the article 14 increases above the thickness of the article for the composite curve 94.

Figure 7:
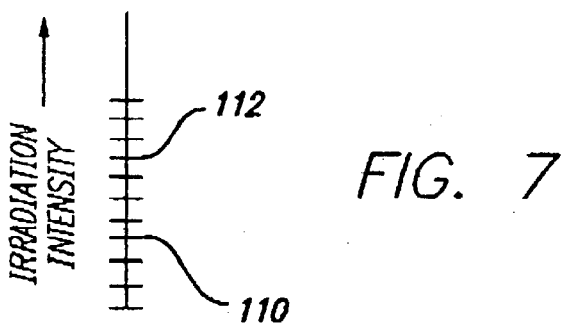
FIG. 7 is a chart showing the minimum and maximum irradiation intensities which are to be produced in the articles at the different positions in the articles.

FIG. 7 is a chart showing the range of irradiation intensities that the system described above should produce. For example, the irradiation system 10 should produce at least a first irradiation dose 110 in FIG. 7 at every position in the article 14 in order to reduce the number of harmful organisms such as *E-Coli*, listeria and salmonella when the article is a beef patty. If the irradiation intensity at any position in the article 14 is below the value 110, the harmful organisms (e.g. *E-Coli*) in the article may not be reduced sufficiently so that a person eating the beef patty can become sick. The radiation intensity should not exceed a second value 112 at every position in the article in order to preserve the life of beneficial organisms in such articles 14 as beef patties. As will be seen, the radiation intensity 112 is greater than the radiation intensity 110.

As will be seen, the difference between the maximum radiation intensity and the minimum radiation intensity at different vertical positions in the article 14 increases with increases in the thickness of the article. It is desirable to maintain this difference within particular limits. On the other hand, it is desirable to maintain the ability of the system 10 to process as thick articles 14 as possible in order to maintain the versatility of the system. Success is accordingly achieved by providing an optimum thickness of the articles 14 at an optimum ratio of the maximum value 112 and the minimum value 110 of the radiation dose throughout the article and by providing these parameters at the lowest cost.

FIG. 11 illustrates another preferred embodiment, generally indicated at 200, of a system disclosed and claimed in co-pending application Ser. No. 09/456,061. However, the system 200 is not as preferred as the system 10. The preferred embodiment 200 shown in FIG. 11 includes a pair of radiation sources 202 and 204 respectively corresponding to the radiation sources 46 and 48 in the embodiment shown in FIGS. 1–4 and described above. The system 200 includes a load conveyor, generally indicated at 208, having a straight portion 208a extending from a loading area 206, a portion 208b having a curvature of substantially 900, a straight portion 208c extending in a direction opposite to the straight portion 208a, a portion 208d having a curvature of substantially 90° and extending in a direction opposite to the curved portion 208b, a straight portion 208e extending in a direction corresponding to the straight portion 208a, a portion 208f having a curvature of substantially 90°, a straight portion 208g extending in the same direction as the straight portion 208c and a portion 208h having a curvature of substantially 90°.

A process conveyor generally indicated at 209 extends from the load conveyor portion 208h in a straight path having a direction corresponding to the load conveyor portion 208a. The radiation sources 202 and 204 are disposed at gaps in the process conveyor 209. A load conveyor generally indicated at 211 extends from the process conveyor 209. The load conveyor 211 has a curved portion 211a, a straight portion 211b, a curved portion 211c, a straight portion 211d, a curved portion 211e, a straight portion 211f, a curved portion 211g and straight portions 211h and 211i. A curved portion may be disposed between the straight portions 211h and 211i. An unloading area 213 may be disposed at the end of the straight portion 211i.

Radiation shielding material, generally indicated at 210, such as concrete envelopes the system 200 to define a chamber. Radiation shielding material 212 such as concrete is disposed within the loop defined by the process conveyor 209, the load conveyor portions 208e–208h and the load conveyor portions 211a–211e to define a wall. A wall 214 made from the radiation shielding material such as concrete extends integrally from the radiation shielding material 212 into the space between the curved portions 208d and 211e. A roof and a floor made from a radiation shielding material such as concrete may also be provided in the embodiment shown in FIG. 11.

The embodiment shown in FIG. 11 appears to have certain disadvantages relative to the embodiment shown in FIGS. 1–4 and described above. It appears to occupy more space than the embodiment shown in FIGS. 1–4. It also appears to require more radiation shielding material than the embodiment shown in FIGS. 1–4. Furthermore, the loading and unloading areas in the embodiment shown in FIG. 11 appear to be significantly removed from each other relative to the positioning of the loading area 12 and the unloading area 56 in the embodiment shown in FIGS. 1–4. This increases the difficulty of transferring the articles 14 between the loading 206 and the unloading area 213 in the embodiment shown in FIG. 11. In view of the above, the embodiment shown in FIGS. 1–4 and described above appears to be the preferred embodiment in comparison to the embodiment 200 in FIG. 11.

Figure 12:
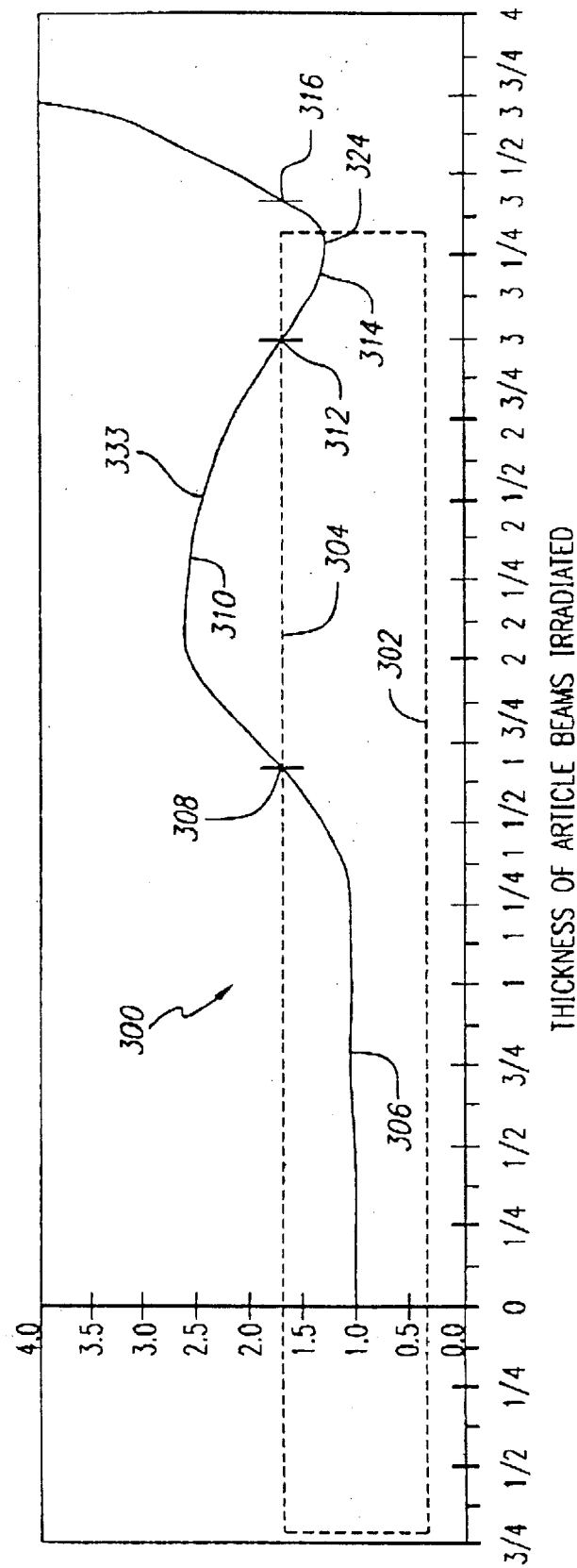
FIG. 12 is a drawing showing the relative amounts of irradiation produced in an article for different thicknesses in the article when the article has progressive thicknesses.

FIG. 12 is a curve, generally indicated at 300, showing on a horizontal axis the thickness in inches of the article 14 (with unit density) being irradiated. The curve 300 also shows on a vertical axis a ratio between the minimum amount of the cumulative radiation at any position in the article 14 and the maximum amount of the cumulative radiation at any position in the article.

A broken line 302 is provided in FIG. 12 to indicate the lowest level at which the cumulative amount of radiation can be provided in the article 14 to kill all of the harmful bacteria in the article. A broken line 304 is provided in FIG. 12 to indicate the highest level at which the cumulative amount of the radiation can be provided in the article 14 without harming the beneficial bacteria in the article. The area in FIG. 12 between the broken lines 302 and 304 constitutes the optimal values for the production of the cumulative amount of irradiation in the article 14 at different thicknesses in the article.

The curve 300 represents empirical data. The curve 300 includes a first portion 306 which extends from a zero (0) thickness to a thickness 308 at which the first portion crosses the broken line 304 to a position above the broken line. This occurs at a thickness of approximately one and five eighth inches (1⅝"). As will be seen in FIG. 12, the first portion 306 is within the area which constitutes the optimal values for the production of the cumulative amount of the irradiation in the article at the different positions in the article.

The curve 300 includes a second portion 310. The portion 310 extends from the article thickness 308 to an article thickness 312 at which the second portion crosses the broken line 304 into the optimal area between the broken lines 302 and 304. This occurs at a thickness of approximately three inches (3"). As will be seen, the second portion 310 provides at each different thickness a cumulative amount of irradiation which is greater than that represented by the broken line 304. This indicates that the cumulative amount of the irradiation is at the level where beneficial bacteria in the article will be destroyed.

The curve 300 includes a third portion 314 which extends from the article thickness 312 to an article thickness 316 at which the third portion intersects the broken line 304 and extends above the broken line 304. This occurs at a thickness of approximately three and three eighths inches (3⅜"). The third portion 314 is within the area which constitutes the optimal value for the production of the cumulative amount of the irradiation in the article.

As will be seen in FIG. 12, it would be desirable to reduce the cumulative amount of the irradiation in the curve portion 310 to a value within the optimal area defined by the broken lines 302 and 304. Preferably this can be accomplished by disposing members 320 and 322 (FIG. 13) respectively between the radiation sources 46 and 48 and the article 14 on the process conveyor 38 in the embodiment shown in FIGS. 1–4. The members 320 and 322 may be made from a suitable material such as a metal. The metal may illustratively be aluminum or copper. The members 320 and 322 are included in the preferred embodiment of this invention.

The members 320 and 322 may be provided with substantially identical characteristics. The members 320 and 322 may be considered as attenuators which reduce the level of the cumulative amount of the irradiation in the article 14 to a magnitude between the broken lines 302 and 304 in FIG. 12. Preferably the members 302 and 304 reduce the cumulative amount of the irradiation in the article 14 to a level indicated at 324 in FIG. 12. This level is desirable because it is further from the broken line 304 than any other thickness in the third portion 314.

Figure 13:
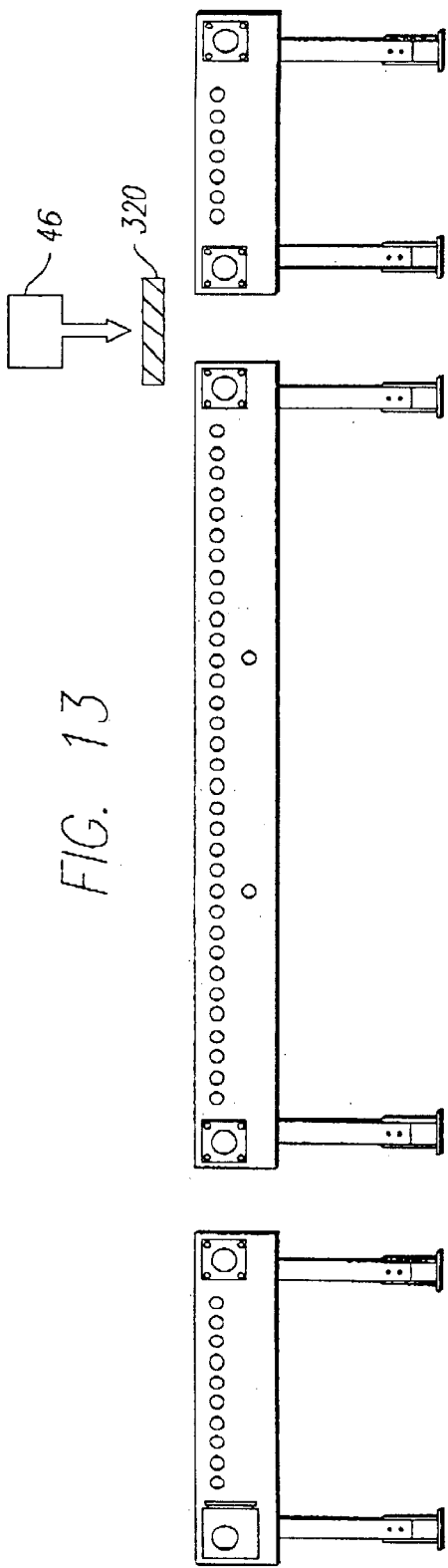
FIG. 13 is a schematic view of a system constituting a preferred embodiment of the invention for irradiating an article with first and second beams respectively disposed on opposite sides of the article and for disposing control members between the beams and the article to maintain the irradiation within the article between optimal limits when the article has a particular range of thicknesses.
Figure 14:
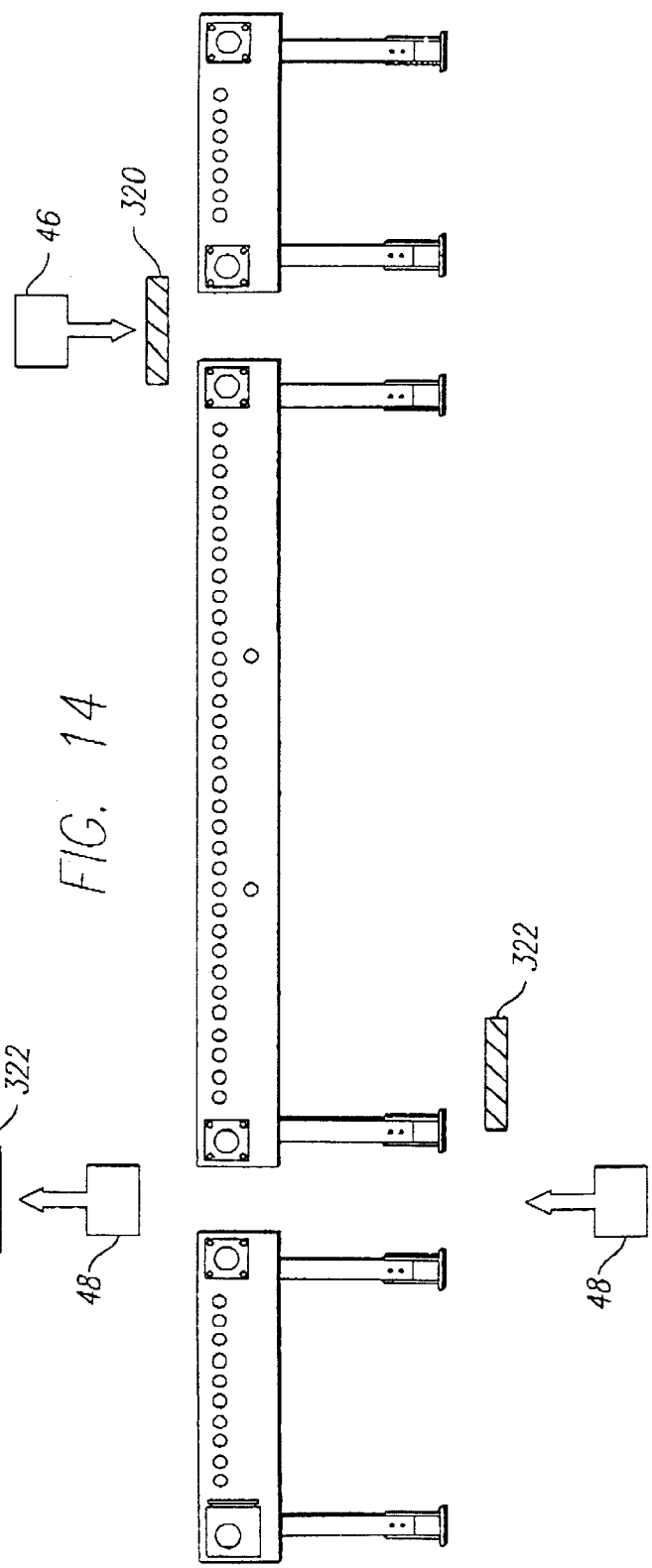
FIG. 14 is a schematic view of a system constituting a preferred embodiment of the invention for irradiating opposite sides of an article with a single beam and for disposing a control member between the beam and the article to maintain the irradiation within the article between the optimal limits when the article has a particular range of thicknesses.

FIG. 14 is a schematic showing similar to the schematic showing in FIG. 13 except that it employs only the member 320 for attenuating the irradiation in the article 14 to the optimal value between the broken lines 302 and 304. This results from the displacement of the member 322 to a position to one side of the beam between the source 48 and the article 14 as shown in FIG. 14. The preferred embodiment of the system shown in FIGS. 13 and 14 is used in conjunction with the system shown in FIGS. 8–11 to attenuate the irradiation in the article 14 to the optimal value between the broken lines 302 and 304 when the thickness of the article 14 is between the positions 308 and 312 in FIG. 12.

Another preferred embodiment of a system constituting this invention and generally indicated at 330 in FIGS. 15 and 16 may be provided for automatically moving the member 320 to a thickness for obtaining the optimal level of the cumulative amount of the irradiation in the article 14 when the thickness of the article 14 is in the second portion 310 of the curve 300. In this system, the member 320 is provided with a particular thickness at progressive incremental positions. The thickness of the member at these particular thicknesses corresponds to the distance of the second portion 310 of the curve 300 above the broken lines 304 at progressive incremental thicknesses along the second portion 310. Each of the progressive incremental positions in the members 320 and 322 may be preferably provided with a width corresponding to the width of the radiation beam from the source 46. This width is indicated at 331 in FIG. 15.

A microprocessor 332 in the system 330 receives information relating to the thickness of the article 14 when the article has a thickness in the second portion 310 of the curve 300. The microprocessor causes the member 320 to move to the incremental position between the source 46 and the article 14 through a distance related to the distance between the beginning 308 of the second portion 310 and the thickness of the article in the second portion 310. For example, the microprocessor 332 may cause the member 320 to move through an incremental distance related to the distance between the beginning 308 of the second portion 310 and a position 333 in FIG. 12 when the article has the thickness or width 335. At this distance, the member 320 may have a thickness to compensate for the amount at the thickness position 333 of the cumulative irradiation above the optimal level 324 of the cumulative irradiation in the third portion 314.

The movement of the member 320 is provided by a pinion gear 334 which rotates in response to commands from the microprocessor 332 to move a rack gear 336 formed at the bottom of the member 320. In this way, the optimal level 324 of the cumulative amount of the irradiation is maintained regardless of the thickness of the article 14 in the second portion 310 of the curve 300.

It will be appreciated to a person of ordinary skill in the art from FIGS. 15 and 16 and from the discussion above that the embodiment shown in FIGS. 15 and 16 can be modified and used in the modified form with the embodiment shown in FIGS. 1–4 to provide the automatic movement of the members 320 and 322 to a desired position. In this desired position, the members 320 and 322 are positioned in the path of the beams from the radiation sources 46 and 48 to the article 14 to reduce the cumulative radiation in the article to an intensity between the broken lines 302 and 304 when the intensity of the radiation would otherwise be above the broken line 304.

Although this invention has been disclosed and illustrated with reference to particular preferred embodiments, the principles involved are susceptible for use in numerous other embodiments which will be apparent to persons of ordinary skill in the art. The invention is, therefore, to be limited only as indicated by the scope of the appended claims.

What is claimed is:

1. A method of irradiating, with an optimal amount of cumulative radiation, an article having first and second opposite sides, including the steps of:

directing radiation to the first side of the articles for the passage of the radiation through the article, rotating the article through an angle of substantially 180° to have the second side of the article face the radiation, thereafter directing the radiation to the second side of the article for the passage of the energy beam through the article, and providing a member in the path of the electron beam with a thickness, dependent upon the thickness of the article, to provide the article with the optimal amount of the cumulative irradiation.

2. A method as set forth in claims 1 wherein the member is disposed in the path of the radiation to the article only when the thickness of the article is between particular limits.

3. A method as set forth in claim 2 wherein the member is provided with a thickness dependent upon the thickness of the article at different positions between the particular limits.

4. A method as set forth in claim 1 wherein the direction of the radiation toward the article provides for an irradiation of the article with the optimal amount of cumulative irradiation for thicknesses of the article to a first value, provides for an irradiation of the article with an amount of cumulative radiation greater than the optimal amount of cumulative radiation for different thicknesses of the article between a first value and a second value greater than the first value and provides for a cumulative irradiation of the article with the optimal amount of cumulative irradiation for thicknesses of the article between the second value and a third value greater than the second value and wherein the member is disposed in the path of the radiation beam, when the thickness of the article is between the first value and the second value, to provide the article with the cumulative amount of irradiation at the optimal value.

5. A method as set forth in claims 4 wherein the member is provided with a thickness, when the thickness of the article is between the first and second values, to provide the article and the member with a combined thickness between the second and third values.

6. A method as set forth in claim 1 wherein the member is provided with a cumulative amount of irradiation, when the thickness of the article is between the first value and the second value, to reduce the cumulative amount of the irradiation in the article to the optimal value.

7. A method of irradiating, with an optimal amount of radiation, an article having first and second opposite sides, including the steps of:

providing radiation for irradiating the article, disposing the article in the path of the radiation, providing a member with different thicknesses at different positions on the member, providing for the disposition, between the radiation and the article, of a portion of the member with a particular thickness dependent upon the thickness of the article, directing the radiation through the member to the first side of the article, rotating the article relative to the radiation through an angle of substantially 180° to have the second side of the article face the radiation after the radiation has been directed through the member to the first side of the article, and thereafter directing the radiation through the member to the second side of the article.

8. A method as set forth in claim 7 wherein the cumulative irradiation received by the article with the first and second sides of the article facing the radiation exceeds the optimal amount of irradiation in a particular range of thicknesses of the article and wherein the member is positioned between the radiation beam and the article in the particular range of thicknesses of the article to reduce the cumulative amount of the irradiation at the article to the optimal amount.

9. A method as set forth in claim 8 wherein the excess of the radiation above the optimal amount is different for different thicknesses of the article in the particular range and wherein the amount of reduction of the cumulative irradiation in the article is varied in accordance with the thickness of the article in the particular range.

10. A method as set forth in claim 7 wherein the member is disposed between the radiation beam and the article only when the particular thickness of the article is within a particular range of values.

11. A method as set forth in claim 10 wherein the member is positioned between the radiation and the article to provide to the radiation a thickness dependent upon the thickness of the article between the first value and the second value.

12. A method as set forth in claim 7 wherein the member is disposed between the radiation and the article only when the thickness of the article is between a first value and a second value and each of the first and second values is greater than zero and the second value is greater than the first value.

13. A method as set forth in claim 7 wherein the optimal amount of the cumulative irradiation is in a particular range of thicknesses of the article greater than the second value and wherein the member is not disposed between the radiation beam and the article when the article has a thickness in the particular range.

14. A method as set forth in claim 7 wherein the optimal amount of the cumulative radiation is in a range of thicknesses of the article less than the first value and wherein the member is not disposed between the radiation beam and the article when the article has a thickness less than the first value.

15. A method as set forth in claim 7 wherein the member is provided with a variable thickness at different positions on the member and wherein the member is positioned relative to the radiation to provide to the radiation a thickness dependent upon the thickness of the article between a first value and a second value where the second value is greater than the first value.

16. A method of irradiating, with an optimal amount of cumulative irradiation, an article having first and second opposite sides, including the steps of:

directing radiation to the opposite sides of the article, and providing a member, in the path of radiation to the article, to reduce the cumulative amount of the irradiation in the article to the optimal amount of the cumulative irradiation, when the amount of the cumulative irradiation in the article would otherwise exceed the optimal amount of the cumulative irradiation.

17. A method as set forth in claim 16 wherein the member is disposed in the path of the radiation to the article only when the thickness of the article is between first and second limits where the second limit is greater than the first limit.

18. A method as set forth in claim 17 wherein each of the first and second limits is greater than zero (0).

19. A method as set forth in claim 18 wherein the member is provided with a thickness dependent upon the thickness of the article at different positions between the first and second limits.

20. A method as set forth in claim 17 wherein the excess of the irradiation above the particular amount is different for different thicknesses of the article between the first and second limits and wherein the amount of reduction of the cumulative irradiation in the article is varied in accordance with the variations in the thickness of the article between the first and second limits.

21. A method as set forth in claim 16 wherein the optimal value of the cumulative amount of the irradiation is provided in the article in a range of thicknesses of the article less than the first limit and wherein the member is not disposed between the radiation beam and the article when the article has a thickness less than the first limit.

22. A method as set forth in claim 16 wherein the member is provided with an individual thickness at different positions on the member and wherein the member is positioned relative to the radiation to provide to the radiation a thickness dependent upon the thickness of the article between the first and second limits.

23. A method as set forth in claim 16 wherein the direction of the radiation toward the article provides for an irradiation in the article with the optimal amount of the cumulative irradiation for thicknesses of the article less than the first limit, provides for an irradiation of the article with an amount of cumulative irradiation greater than the optimal amount of the cumulative irradiation for different thicknesses of the article between the first and second limits and provides for a cumulative irradiation of the article with the optimal amount of the cumulative irradiation for thicknesses of the article between the second limit and a third limit greater than the second limit and wherein the member is disposed in the path of the radiation, when the thickness of the article is between the first and second limits, to provide the article with the optimal amount of the cumulative irradiation.

24. A system for irradiating, with an optimal amount of cumulative radiation, an article having first and second opposite sides, including apparatus for providing radiation, a loading area, an unloading area, a conveyor for transporting the article from the loading area past the radiation apparatus to the unloading area for an irradiation of the first and second sides of the article by the radiation apparatus, the article being constructed to receive the optimal amount of the cumulative irradiation for first thicknesses of the article and to receive greater than the optimal amount of the cumulative irradiation for second thicknesses of the article greater than the first thicknesses, and a member having first and second positions and disposed in the first position for the first thicknesses of the article to provide for the irradiation of the article by the radiation apparatus without any passage of the radiation through the member and disposed in the second position to provide, for the second thicknesses of the article, for the irradiation of the article by the radiation apparatus after the passage of the irradiation through the member to reduce the cumulative amount of the irradiation in the article to the optimal value.

25. A system as set forth in claim 24, including, apparatus for positioning the member to the first position for the first thicknesses of the article and to the second position for the second thicknesses of the article.

26. A system as set forth in claim 24, including, the member being provided with a thickness in the second position to reduce the cumulative irradiation in the article from an amount above the optimal value to the optimal value.

27. A system as set forth in claim 24 wherein the article is constructed to provide individual amounts of irradiation greater than the optimal value for individual positions in the second thicknesses of the article and wherein the member is constructed to receive individual amounts of the cumulative irradiation at individual ones of the second positions of the member to reduce the cumulative radiations in the individual positions in the second thicknesses of the article to the optimal value.

28. A system as set forth in claim 24 wherein the article is constructed to receive individual amounts of cumulative irradiation greater than the optimal value at individual positions in the second thicknesses of the article when the member is not disposed in the path of the radiation from the radiation apparatus to the article and wherein the member is constructed to receive individual amounts of irradiation at individual thicknesses in the second positions of the member and is disposed relative to the radiation apparatus and the article at the individual positions in the second thicknesses of the member to reduce the cumulative irradiation in the second thicknesses of the article to the optimal amount.

29. A system as set forth in claim 28 wherein apparatus is provided for the member to position the member to the first position for the first thicknesses of the article and to individual ones of the second positions for individual ones of the second thicknesses of the article to reduce the cumulative irradiation at the second thicknesses of the article to the optimal amount.

30. A system for irradiating, with an optimal amount of cumulative irradiation, an article having first and second opposite sides, including a source of radiation, a loading area, an unloading area, a conveyor for transporting the article from the loading area past the radiation source for an irradiation of the first side of the article by the radiation source, a mechanism for rotating the article through an angle of 180° after the irradiation of the first side of the article by the radiation source and for introducing the rotated article to the conveyor for the transport of the article past the radiation source to the unloading area and for the irradiation of the second side of the article by the radiation source during such or any port, the article being of a size to receive a cumulative amount of radiation greater than the optimal amount, and a member positionable between the radiation source and the conveyor for reducing to the optimal amount the cumulative amount of irradiation introduced to the first and second sides of the article when the article has a size to receive a cumulative amount of irradiation greater than the optimal amount.

31. A system as set forth in claim 30 wherein
the article has first, second and third ranges of thicknesses and wherein
   the article receives the optimal amount of the cumulative irradiation at the first and third ranges of thicknesses and receives cumulative irradiations greater than the optimal amount at the second range of thicknesses and where the second range of thicknesses is between the first and third ranges of thicknesses and where
the member is positioned between the radiation source and the article in the second range of thicknesses of the article to reduce the cumulative radiation in the article to the optimal amount.

32. A system as set forth in claim 31 wherein
the article receives individual amounts of cumulative irradiation at different thicknesses in the second range and where
the member has individual thicknesses for the different thicknesses of the article in the second range to reduce the cumulative irradiation in the article to the optimal amount for the different thicknesses of the article in the second range.

33. A system as set forth in claim 31 wherein
the member is disposed in the path of the radiation from the radiation source to the article in the second range of thicknesses of the article to reduce the cumulative irradiation in the article to the optimal amount and wherein
the member is disposed in the first and third ranges of thickness of the article to have no effect on the cumulative irradiation in the article.

\* \* \* \* \*